US00PP26179P3

(12) United States Plant Patent
Sheehan

(10) Patent No.: US PP26,179 P3
(45) Date of Patent: Dec. 1, 2015

(54) GRAPEVINE 'SHEEGENE-22'

(50) Latin Name: *Vitis vinifera*
Varietal Denomination: Sheegene-22

(71) Applicant: Sheehan Genetics, LLC, Fresno, CA (US)

(72) Inventor: Timothy P. Sheehan, Vancouver, WA (US)

(73) Assignee: Sheehan Genetics, LLC, Fresno, CA (US)

( * ) Notice: Subject to any disclaimer, the term of this patent is extended or adjusted under 35 U.S.C. 154(b) by 180 days.

(21) Appl. No.: 13/998,363

(22) Filed: Oct. 25, 2013

(65) Prior Publication Data

US 2015/0121579 P1 Apr. 30, 2015

(51) Int. Cl.
*A01H 5/08* (2006.01)

(52) U.S. Cl.
USPC ..... Plt./205

(58) Field of Classification Search
USPC ..... Plt./205
See application file for complete search history.

(56) References Cited

U.S. PATENT DOCUMENTS

| | | | |
|---|---|---|---|
| PP4,787 | P | 11/1981 | Olmo et al. |
| PP9,865 | P | 4/1997 | Ralli et al. |
| PP18,937 | P2 | 6/2008 | Sheehan |
| PP18,959 | P2 | 6/2008 | Sheehan |
| PP18,960 | P2 | 6/2008 | Sheehan |
| PP18,987 | P2 | 6/2008 | Sheehan |
| PP19,041 | P2 | 7/2008 | Sheehan |
| PP19,911 | P2 | 4/2009 | Sheehan |
| PP19,912 | P2 | 4/2009 | Sheehan |
| PP20,110 | P3 | 6/2009 | Sheehan |
| PP20,236 | P3 | 8/2009 | Sheehan |
| PP20,252 | P3 | 9/2009 | Sheehan |
| PP20,281 | P3 | 9/2009 | Sheehan |
| PP20,317 | P3 | 9/2009 | Sheehan |
| PP20,753 | P3 | 2/2010 | Sheehan |
| PP21,316 | P3 | 9/2010 | Sheehan |
| PP23,125 | P2 | 10/2012 | Sheehan |
| PP23,837 | P3 | 8/2013 | Sheehan |
| PP25,095 | P3 | 11/2014 | Sheehan |
| PP25,131 | P3 | 12/2014 | Sheehan |
| 2008/0201809 | P1 | 8/2008 | Sheehan |
| 2013/0276181 | P1 | 10/2013 | Sheehan |

OTHER PUBLICATIONS

U.S. Appl. No. 14/121,181, filed Aug. 8, 2014, Sheehan.

*Primary Examiner* — Anne Grunberg
(74) *Attorney, Agent, or Firm* — Dentons US LLP

(57) ABSTRACT

A new and distinct variety of grapevine characterized by the production of medium, red-colored seeded grapes that mature in early September, approximately two to three weeks later than 'Red Globe' (U.S. Plant Pat. No. 4,787) when grown in the San Joaquin Valley of Central California. The grapes of this new variety are produced on strong woody stems and branches and are well adapted to commercial handling.

1 Drawing Sheet

Latin name of the genius and species of the plant claimed: The claimed plant relates to a new and distinct variety of *Vitis vinifera* to be known as 'Sheegene-22'.

CROSS REFERENCE TO RELATED APPLICATIONS

The claimed plant is not subject of a related application.

STATEMENT OF ANY FEDERALLY-SPONSORED RESEARCH AND DEVELOPMENT

The claimed plant is not subject of Federally-sponsored research or development.

VARIETY DENOMINATION

The new variety of *Vitis vinifera* is the result of hybridization of 'Princess' (unpatented), the pollen parent, with 'Red Globe' (U.S. Plant Pat. No. 4,787), the seed parent, in Spring 2000 at Porterville, Calif. The new variety was first planted in Spring 2001 at Fowler, Calif. The new variety was asexually propagated in Fowler, Calif., in Spring 2010 and grafted on to 'Freedom' virus-free, rootstock. Two hundred grapevines of the new variety were planted in a variety lot block of *Vitis vinifera* located approximately fifteen miles south and west of Fresno, Calif., on the southwest side of Henderson Road. The new variety has been shown to maintain its distinguishing characteristics through asexual propagation.

The new variety is distinguished from its pollen parent, 'Princess' (unpatented), in that the new variety produces red-colored seeded grapes, as compared to the white-colored seedless grapes produced by its pollen parent, 'Princess' (unpatented). The new variety is distinguished from its seed parent, 'Red Globe' (U.S. Plant Pat. No. 4,787), in that the new variety produces medium sized red-colored seeded grapes, as compared to its seed parent, 'Red Globe' (U.S. Plant Pat. No. 4,787), that produces exceptionally large red-colored seeded grapes.

BACKGROUND OF THE INVENTION

The present invention relates to a new and distinct variety of grapevine that produces a medium, red-colored seeded grape that matures during early September when grown in the San Joaquin Valley of Central California.

SUMMARY OF THE INVENTION

The 'Sheegene-22' grapevine is characterized by producing a medium, red-colored seeded grape that has good flavor and it is productive and mature for harvesting and shipment in early September when grown in the San Joaquin Valley of Central California. The new variety can be compared to 'Red Globe' (U.S. Plant Pat. No. 4,787) but the grapes produced by the new variety mature approximately two to three weeks later and are medium in size, among other distinguishing characteristics.

BRIEF DESCRIPTION OF THE DRAWING

The accompanying drawing is a color photograph that displays, across the top, a terminal shoot with leaves and tendrils; immediately below on the left are two small grape clusters with peduncles. To the right and below the small grape clusters are several tendrils. In the center position is a large grape cluster with peduncle. To the left of the large cluster are three grapes on a modified tendril and below the large cluster is a mature leaf displaying the lower surface view. To the right are two grape berries, the berry on the left is cut in half transverse to the longitudinal axis and the berry on the right is cut longitudinally with both berries displaying flesh tissues. To the far right is a mature grape leaf displaying the upper surface view and along the right margin is a mature cane displaying buds. Along the bottom are two immature leaves with the leaf on the left displaying the upper surface view and the leaf on the right displaying the lower surface view.

DETAILED BOTANICAL DESCRIPTION

Referring more to the horticultural description of the new and distinct variety of grapevine, the following has been observed under the ecological conditions prevailing at the origin vineyard located near Fresno, Calif., in the San Joaquin Valley of Central California. All major color descriptions are by reference to the Dictionary of Color by Maerz & Paul, First Edition, published in 1930, unless otherwise noted. Common colors names are also used in several instances.

Vine:

*Size.*—Large for three-year old vine.
*Vigor.*—Very good.
*Chilling requirements.*—Normal for grapevines in the lower San Joaquin Valley of Central California.
*Regularity of bearing.*—Regular.

Trunk:

*Size.*—Medium; 5 in. [12.7 cm] in circumference, 26 in. [66.0 cm] above soil surface.
*Surface texture.*—Rough, shaggy.
*Color of bark.*—P1.8 J8 Domingo (Three year old wood).
*Mature cane color.*—P1.7 El0 Chestnut Brown Stone.
*Length between nodes.*—1½ to 4 in. [3.81 to 10.16 cm].
*Lenticels.*—Numbers: 0.
*Lenticels.* —Size: 0.
*Shoot length.*—2½ to 5½ in. [6.35 to 13.97 cm].
*Shoot shape.*—Semi drooping.
*Tendrils.*—Number: 1 at most. Tendrils length: Medium; 1¾ to 5 in. [4.5 to 12.7 cm].
*Tendrils.*—Form: Trifurcate — occasionally bifurcate.
*Bud shape.*—Simple convex.
*Bud size.*—Small, 0.24 to 0.28 in. [6 to 7 mm] in width.
*Bud fullness.*—Good.

Canes:

*Size.*—Medium.
*Width.*—9 mm [0.354 in] measured 6 nodes from proximal end of cane.
*Cordons.*—30 in. [76.2 cm] (east side) and 35 in. [88.9 cm] (west side).
*Color.*—One year old wood: P1.7 El0 Chestnut Brown Stone.
*Color.*—Immature Branches: P1.20 K6 Pigment G+.

Leaves:

*Description.*—5 lobes; upper lateral sinus vary from shallow to moderately deep and open; lower lateral sinus are mostly deep and closed.
*Size.*—Medium.
*Density.*—Moderate.
*Average length.*—Approximately 4.7 in. [12 cm] without stem.
*Average width.*—6.3 in. [16 cm].
*Form.*—Pentagonal.
*Texture.*—Upper surface: Smooth.
*Texture.*—Lower surface: Slightly rough.
*Color.*—Upward disposed surface: P1.23 J7 Mt. Vernon gr.
*Color.*—Downward disposed surface): P1.21 17 Fern.
*Leaf vein.*—Color: P1.21 17 close to Fern.
*Marginal form.*—Generally undulate.
*Margin.*—Teeth irregular, both sides are convex.
*Petiole size.*—Medium.
*Petiole length.*—3½ to 5 in. [8.89 to 12.7 cm].
*Petiole thickness.*—0.08 in. [2 mm].
*Petiole color.*—P1.19 L5 Cosse GR.
*Petiole color* (*upper surface*).—P1.16 L8 Dark Cardinal.
*Petiole sinus form.*—Open.

Inflorescence:

*General description and location.*—First floral cluster is five nodes from shoot origin. Clusters are small and narrow with very few tendrils. Flower density is medium high.
*Length.*—5.12 to 9.45 in. [13.005 to 24.003 cm] (not including peduncle).
*Width.*—2.36 to 6.69 in. [6 to 17 cm] (first two laterals).
*Peduncle* (*length*).—5.12 to 9.45 in. [13.005 to 24.003 cm].
*Peduncle* (*width*).—0.18 in. [4.5 mm].
*Inflorescences.*—Hermaphroditic.
*Quantity per cluster.*—200 to 400.

Flowers:

*Flower buds.*—Normal.
*Flower buds surface.*—Glabrous.
*Date of bloom.*—April 26.
*Date of full bloom.*—May 1.
*Size.*—0.12 in. [3 mm].
*Petals* (*color*).—5GY 5/8 (Munsell Color Charts for Plant Tissues).
*Petals* (*size*).—0.08 in. [2 mm] (5 segments, complete separation).
*Stamens.*—0.08 in. [2 mm] in length; upright.
*Anthers.*—Normal; creamy in color.
*Calyptra.*—5 segments, complete separation. Calyptra — Color: 5GY 5/8 (Munsell Color Charts for Plant Tissues).

*Amount of pollen.*—Moderate; yellowish-white.
*Date of visible berry set.*—May 9.
*Size of berries.*—Normal.

Fruit:
*Solids.*—20.0 Brix.
*Acids.*—0.27.
*Sugar/acid ratio.*—74.
*Juice pH.*—4.00.
*Seeds.*—Three to four.
*Capstem pedicel.*—8 to 10 mm [0.31 to 0.39 in.] long; 2 mm [0.08 in.] wide.
*Berry weight.*—5.0 grams [0.18 oz.].
*Juice color.*—Clear.
*Cluster shape.*—Conical.
*Cluster average length* (*not including stem*).—8 to 9 in. [20.32 to 22.86 cm].
*Cluster average diameter.*—5.220 to 6.25 in. [13.26 to 15.875 cm].
*Cluster average weight.*—425 to 600 grams [14.99 to 21.16 oz.].
*Compactness.*—Medium.
*Peduncle length.*—4 to 5 cm. [1.57 to 1.97 in.].
*Peduncle diameter.*—5 to 7 mm. [0.20 to 0.28 in.].
*Berry size.*—Medium.
*Berry form.*—Broad ellipsoid.
*Berry numbers.*—85 to 120 berries per cluster.
*Berry size* (*length*).—0.98 to 1.22 in. [25 to 31 mm].
*Berry size* (*width*).—0.91 to 1.06 in. [23 to 27 mm].

Skin:
*Skin thickness.*—Medium.
*Texture.*—Semi-tough.
*Blush color.*—P1.55 L8 Robient.
*Pulp.*—Clear.
*Lenticels.*—Present.

Flesh:
*Flesh color.*—P1.46 K11 Petunia.
*Juice production.*—Moderate.
*Flavor.*—Sweet and neutral.
*Fragrance.*—Absent.
*Texture.*—Firm.
*Use.*—Fresh Market.
*Keeping quality.*—Good.
*Resistance to disease.*—Unknown.
*Harvesting.*—Early September in the San Joaquin Valley of Central California.
*Shipping and handling qualities.*—Very good.

Although the new variety of grapevine possesses the described characteristics noted above as a result of the growing conditions prevailing in the San Joaquin Valley of Central California, it is to be understood that variations of the usual magnitude and characteristics incident to changes in growing conditions, irrigation, fertilization, pruning, pest control, climatic variations, and the like, are to be expected.

Having thus described and illustrated our new variety of grapevine, I claim:

1. A new and distinct variety of grapevine, substantially as described and illustrated herein.

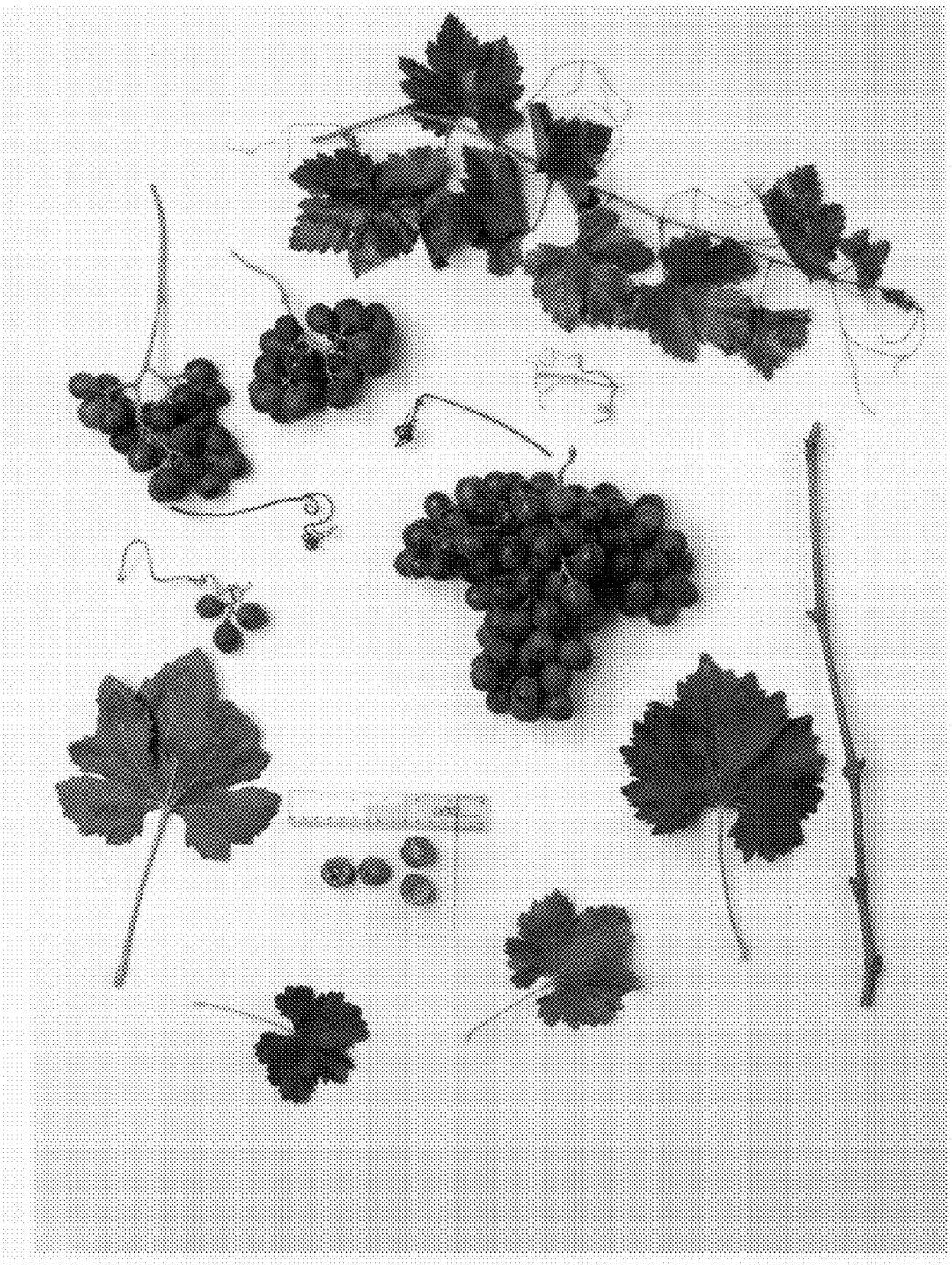

* * * * *